United States Patent [19]
Yeh

[11] Patent Number: 4,787,379
[45] Date of Patent: Nov. 29, 1988

[54] HERNIA HEALING TRUSS

[76] Inventor: Bo-Wung Yeh, No. 14, Lane 200, Guaang Dung Road, Ping Dung City, Taiwan

[21] Appl. No.: 42,443

[22] Filed: Apr. 24, 1987

[51] Int. Cl.$^4$ ............................................. A61F 5/24
[52] U.S. Cl. ................................. 128/95.1; 128/96.1; 128/101.1; 128/105.1; 128/106.1; 128/117.1; 128/120.1
[58] Field of Search ............ 128/95.1, 96.1, 97.1, 128/98.1, 99.1, 100.1, 101.1, 102.1, 103.1, 106.1, 107.1, 108.1, 109.1, 110.1, 111.1, 112.1, 117.1, 120.1, 123.1, 157, 113.1; 24/31 H, 31 W, 33 A, 33 F, 471, 472, 474, 476

[56] References Cited

U.S. PATENT DOCUMENTS

| | | | |
|---|---|---|---|
| 1,399,386 | 12/1921 | Husar | 128/96.1 |
| 1,486,021 | 3/1924 | Johnson | 128/120.1 |
| 2,522,056 | 9/1950 | O'brien | 128/96.1 |
| 2,678,042 | 5/1954 | De Mott | 128/112.1 |
| 3,532,090 | 10/1970 | Ward et al. | 128/95.1 |

*Primary Examiner*—Richard J. Apley
*Assistant Examiner*—Paul B. Prebilis
*Attorney, Agent, or Firm*—Morton J. Rosenberg

[57] ABSTRACT

This invention is related to a hernia healing truss which is a belt with a flexible and bendable metal spring sheet inside. On one end of the belt, there is a pad, while on the other end, there is an elastic band and an inverted "U" shaped metal hook to hook the pad on the end of the belt. A belt is provided to wrap the patients' waist and legs which can be directly affixed to the soft belt so as to bind the waist of the patients.

4 Claims, 4 Drawing Sheets

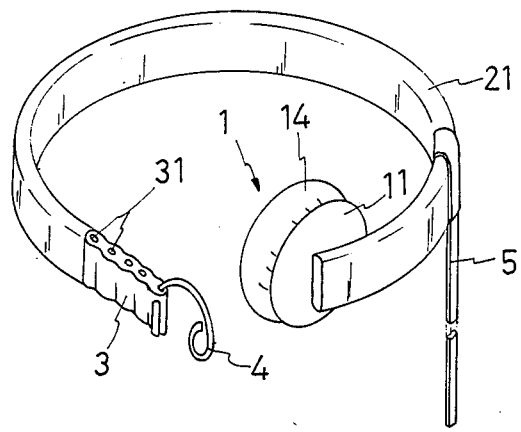
F I G. 2.
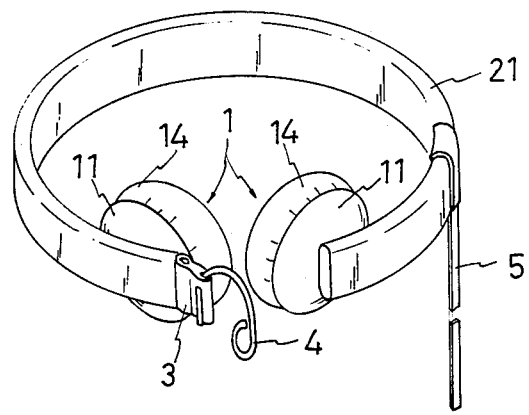
F I G. 3.

HERNIA HEALING TRUSS

BACKGROUND OF THE INVENTION

FIELD OF THE INVENTION

The invention is a structure concerning hernia healing trusses. The currently used hernia bandages by various Countries of the World are generally sorted into categories, as illustrated in following paragraphs:

Rubber trusses are generally used in Taiwan, Japan and other Countries. The shortcoming thereof is that the rubber trusses are too tight in the waist, thus the strength cannot be concentrated at the suffering spot and the hernias cannot be entirely braced back into the abdomen; therefore, a falling or dropping is occasionally seen. The frequent use of such rubber trusses hurts the skin because of the contact with the skin especially when used for children.

Canvas bandage having an elastic band inside is generally used in U.S.A., Canada and Australia. The outlook thereof is better and it is less abrasive to the skin, but the other shortcomings are similar to the rubber trusses, i.e. causing the user to feel sultry and incapable of providing sufficient strength.

Spring trusses are generally used in West Germany, Japan, and other Countries. The strength applied to the suffering spot is strong, and so it is only good for minor hernias and ineffective for serious hernias. Even if it is used for minor hernias, the patients activities such as crouching, sitting and standing will cause gaps and openings on the suffering spots; therefore, a falling or dropping is also occasionally seen. This is a major reason why hernias never heal when using this type of truss. Thus, the purpose of the present invention is to correct all the short-comings of the traditional hernia truss to achieve a perfect treatment thereto.

SUMMARY OF THE INVENTION

A hernia healing truss is herein described including a buckel to wrap a sponge with soft cloth and encircle an exterior portion of a fixing plate. Such is covered wtih a hood and is coupled to a soft belt formed of a soft leather and wrapped with cotton having a flexible metal spring sheet approximating four-fifths the length of the total belt and connected with a buckle on one end and an elastic band on the other end. The elastic band is seamed into a plurality of compartments to be hooked by a metal hook. A wrapping bandage formed of soft cloth strips is coupled on the end of the buckle to bind the legs and waists of the patients.

The overall system includes a simple model which is suitable for one-year old children for left or right side use and includes a model suitable for patients with hernias on two sides. A practical model is usable for one year old babies to aged male or female patients for use on either the left or right sides. Such practical models are especially useful for those who have to work or move extensively. An intensified model is further provided and designed for those who must do hard labor or vigorous exercise and adds twice the length of cloth envelopes to a soft belt portion when taken with respect to the practical model.

BRIEF DESCRIPTION OF THE DRAWINGS

FIG. 2 is a perspective drawing of the practical model of the subject invention;

FIG. 3 is a perspective drawing of an embodiment of the practical model of the subject invention concept;

DESCRIPTION OF THE PREFERRED EMBODIMENTS

Figure 1:
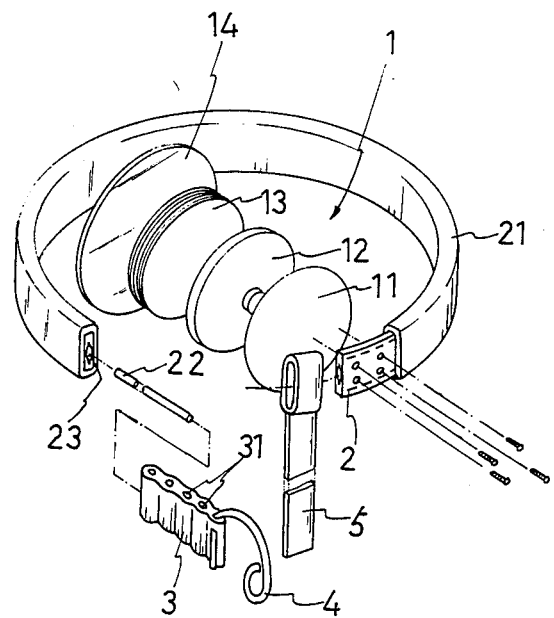
FIG. 1 is a perspective blow out drawing of the preferred embodiment of the subject invention concept directed to the practical model.

Referring to FIGS. 1 and 2, there is shown the practical model of the subject hernia truss system suitable for general use. A belt is composed of a pad 1, a soft belt 2, an elastic belt 3, a metal hook 4, and a strip wrapping belt or auxiliary bandage 5.

Pad 1 includes a hood 11, a fixing plate 12, a sponge 13, and a strip of wrapping cloth 14.

In order to assemble the subject system shown in FIGS. 1 and 2, wrapping cloth 14 wraps sponge 13 and such is fixed in the outside of fixing plate 12 and then covered with hood 11. Pad 1 of this system may serve the purposes of pressing the treatment spot. The design of sponge 13 and wrapping cloth 14 enables the skin of the portion being impinged to feel comfortable buffering effects, furthermore, such absorbs sweat and advantageously ventilates the treatment area.

Belt 2 is formed of a soft leather which is seamed into a vacuum state and then wrapped with cotton cloth 21. Such is laid inside of belt 2 with the flexible and bendable metal spring sheet 22 whose length is approximately 4/5ths of the main body of the system, with one of its ends used to connect pad 1 and the other to connect elastic band 3. The length of the elastic band is approximately 1/5th of the main body of the system and such connects soft belt 2 to integrate the main body of the system.

With use of the soft cotton cloth 21, there is an advantageous attaching to the skin of the patients' waists. The design of the metal spring sheet 22 affixed to the patients' waists, can be adjusted in accordance with the size of the patients' waists to bring the effects of press and brace into full play. The word "press" refers to the wrapping method of the minor hernia horizontal treatment, while the word "brace" refers to the wrapping method of a serious hernia bracing from the inside portion of the thigh upward.

The elastic band 3 is coupled with the other end of the soft belt 2 between the belt and the pad 1 such that elements 1, 2, and 3 constitute a buckle means. The elastic band 3 is seamed into several compartments 31 which enable a metal hook to adjust its tightness as required to achieve the treatment effect. To match the expansion strengh of the elastic band 3, the metal hooks on the belt 1 affix it to the proper position.

The wrapping trusses 5 is made of a cotton cloth strip which is fixed in the end of the belt to be ready to bind on the leg or the waist of the patients to fixed position for increased protection. The practical model in principle is suitable for left side or right side hernias of different patients, due to the fact that the round pad 1 is suitable for either side. Additionally, the metal hook 4 may be disposed in reverse position so that the hook can engage with the pad 1 in an up-to-down location.

Figure 4:
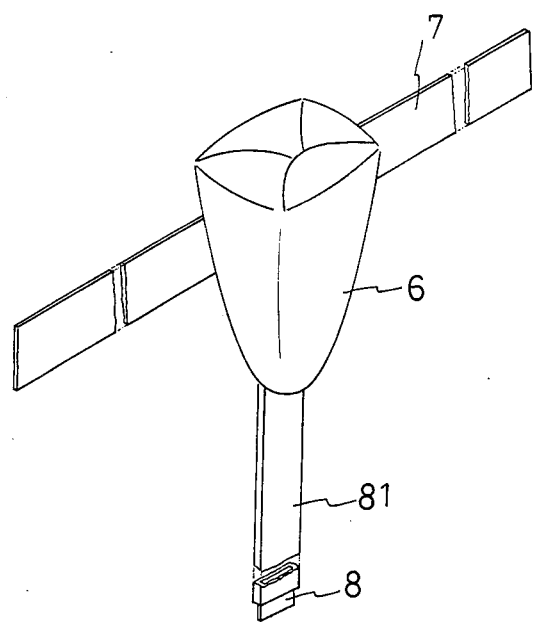
FIG. 4 is a perspective view of the simple model of the subject invention concept.
Figure 5:
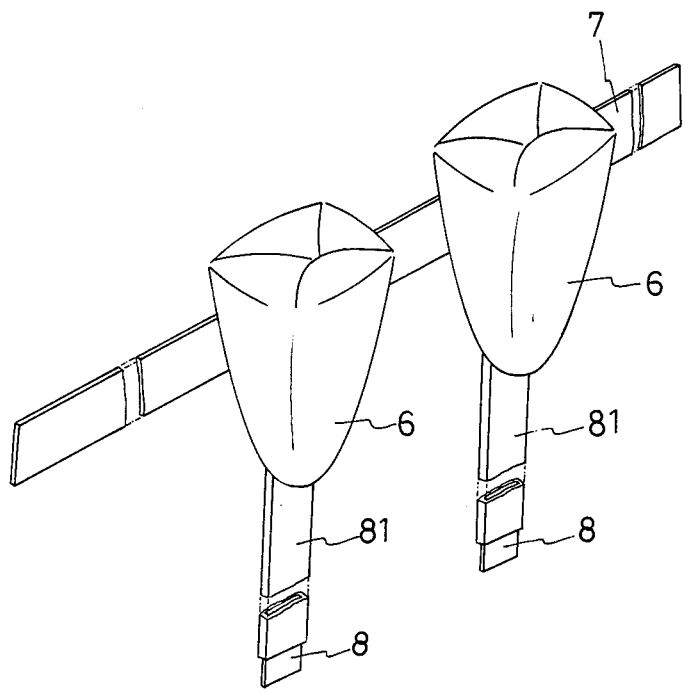
FIG. 5 is a perspective drawing of the simple model of the subject invention concept showing use for hernias on two sides of a patient; and, FIG. 6 is a perspective drawing of an embodiment of the subject invention concept showing the intensified model of the hernia healing truss system.

Referring now to FIGS. 4 and 5, there is shown the simple model of the subject invention concept where the belt includes the pad 6, soft belt 7, elastic band 8, and the cloth envelope 81.

The pad 6 is filled with buffering fillings and the pad 6 is enlarged in the upper portion and smaller in the lower portion in a reverse cone shape. Such is directly seamed on the soft belt 7 and an elastic band 8 is stitched to the bottom of the buckle 6 and is used to bind the leg to auxiliary fix the proper location.

If the patient suffers on both sides, the pad 6 may be two pads to be used for both sides.

Figure 6:
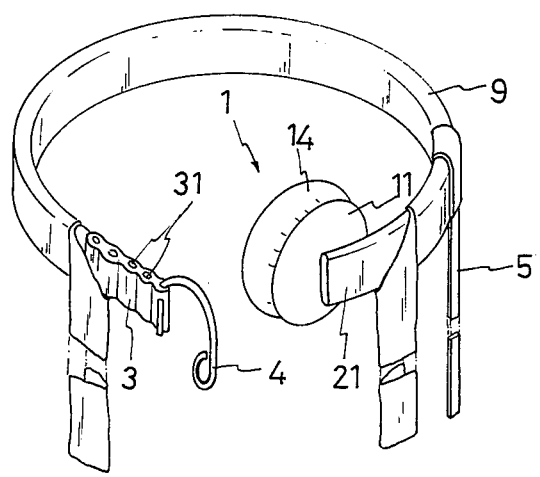

Referring to FIG. 6, there is shown the intensified model of the subject invention concept which is used to connect twice the length of cloth envelope on a soft belt of the practical model to fix the area being treated with a higher force in order to allow the patients to do increased labor or vigorous exercise and achieve the treating effect.

I claim:

1. A hernia healing truss for use by a patient, comprising:

belt means for coupling and positionally locating said truss on said patient, said belt means including a flexible metal spring extending longitudinally through a substantial portion thereof; said flexible metal spring being overlaid by (1) a first covering layer formed of a soft leather composition, and (2) a second covering layer formed of a cotton textile composition, said belt means further including an elastic band member of predetermined length coupled to said flexible metal spring and having a plurality of compartments disposed along said length for receiving a coupling hook member;

a coupling hook member engaging one of said compartments first buckle means coupled to said flexible metal spring for (1) applying pressure to a first hernia site, and (2) receiving said coupling hook member for forming a releasable coupling therewith, said first buckle means including a pad member which comprises a sponge member covered by a soft cloth member, said pad member being fixedly coupled to a fixing plate member, said fixing plate member being covered by a hood member and fixedly coupled to said flexible metal spring; and, a wrapping belt member formed of a soft cloth material composition and being positionally located adjacent said first buckle means for binding to said patients legs and waist.

2. The hernia healing truss as recited in claim 1, wherein said truss includes a second pad member for applying pressure to a second hernia site, said flexible metal spring being fixedly coupled to said first and second buckle means on opposing ends thereof.

3. The hernia healing truss as recited in claim 1, wherein said second covering layer extends substantially beyond said first covering layer at opposing ends of said belt means for use by patients performing strenuous labor and vigorous exercises.

4. The hernia healing truss as recited in claim 1, wherein said pad member has a substantially conical contour extending from an upper portion of predetermined dimension to a lower portion having a predetermined dimension less than said upper portion, said pad member being coupled to said wrapping belt member for use by a child patient.

* * * * *